United States Patent [19]

Bowman et al.

[11] Patent Number: 5,026,651
[45] Date of Patent: Jun. 25, 1991

[54] METHODS AND COMPOSITIONS FOR THE PRODUCTION OF HUMAN TRANSFERRIN

[75] Inventors: Barbara H. Bowman; Funmei Yang, both of San Antonio, Tex.

[73] Assignee: Board of Regents, The University of Texas System, Austin, Tex.

[21] Appl. No.: 727,335

[22] Filed: Apr. 25, 1985

[51] Int. Cl.$^5$ .................... C12N 15/00; C12N 1/20; C12P 19/34; C12P 21/02; C07H 15/12

[52] U.S. Cl. .................... 435/320.1; 435/91; 435/172.3; 435/252.33; 435/317.1; 435/69.1; 435/71.1; 536/27

[58] Field of Search .................... 435/172.3, 317, 253, 435/320; 536/27; 935/9, 11

[56] References Cited

PUBLICATIONS

Schaeffer et al., Gene, vol. 56, pp. 109–116 (1987).

Blattner et al., Science, vol. 196, pp. 161–169.

*Primary Examiner*—Charles F. Warren
*Assistant Examiner*—Christopher Low
*Attorney, Agent, or Firm*—Arnold, White & Durkee

[57] ABSTRACT

The present invention discloses the isolation and nucleic acid sequence of a cDNA recombinant plasmid insert which contains the entire coding sequence for the human transferrin protein. The predicted amino acid sequence of human transferrin is disclosed as well. The cDNA-bearing recombinant plasmid was selected from a human recombinant clone bank constructed in the plasmid pKT218, a derivative of pBR322. Also disclosed are proposed methods and compositions for constructing a recombinant expression vector whereby one may obtain expression of the recombinant human transferrin protein.

16 Claims, No Drawings

METHODS AND COMPOSITIONS FOR THE PRODUCTION OF HUMAN TRANSFERRIN

BACKGROUND OF THE INVENTION

The Government may own certain rights in this invention pursuant to NIH grant numbers HD16584 and GM33298.

The present invention discloses the use of recombinant DNA technology to clone and sequence the gene for human transferrin and, more particularly, the use of this cloned gene in the production of recombinant human transferrin, an iron-binding serum protein.

In human and other vertebrates, iron transport and storage are carried out by transferrin and ferritin. Transferrin-like molecules are relatively new in evolution, being seen only in chordates, while ferritin is present in all plant and animal cells. The family of iron-binding proteins appear to share properties in humans, rabbits and chickens.

Human transferrin carries iron from the intestine, reticuloendothelial system, and liver parenchymal cells to all proliferating cells in the body. Cells grown in tissue culture have a similar iron requirement and therefore require transferrin as well. Transferrin has generally been supplied to tissue culture cells by supplementing the tissue culture medium with bovine or fetal bovine serum or by the addition of transferrin which has been isolated from these and other sources. However, animal sera are expensive and ill-defined in that they often include numerous unknown hormones and growth factors which may be undesirable in the tissue culture medium. In that tissue culture is rapidly becoming an important means of supplying medicinal and investigative reagents, it is important that scientists and technologists eventually be able to totally control the growth environment created by tissue culture medium. Such control requires the availability of large quantities of relatively pure growth factors and hormones which may be used to supplement growth medium without resorting to the addition of ill-defined animal serum. In this manner, tissue culture medium may be "tailor-made" in order to achieve the particular growth conditions desired.

Transferrin is presently included in tissue culture in the form of isolated transferrin or animal serum. Isolated transferrin is generally purified from animal livers or serum. However, for the growth of human cells in culture, it is generally preferable to use human Transferrin. Human transferrin has been isolated from certain human tumors grown in culture. However, this source is impractical for providing large quantities of the protein. Accordingly, a method with the potential for isolating commercial quantities of relatively pure human transferrin would be useful.

SUMMARY OF THE INVENTION

The present invention discloses a technique suitable for the construction of recombinant DNA transfer vectors which contain a DNA sequence corresponding to the nucleic acid sequence which codes for the human Transferrin. In addition, the present invention discloses a method for producing genetically engineered Transferrin utilizing recombinant nucleic acid sequences which code for human Transferrin. These sequences will generally be referred to as the recombinant human Transferrin gene.

Genetically engineered Transferrin is produced by providing a cellular clone containing a recombinant DNA expression vector, wherein the expression vector contains a DNA sequence which is complementary to a nucleic acid sequence which codes for human Transferrin, and culturing the cellular clone under suitable conditions to promote the transcription and translation of the recombinant human Transferrin gene into human Transferrin. A recombinant DNA expression vector as used herein refers to a cloning vector, such as the pIN-III vector described in Example III herein, which has been particularly adapted for expressing the protein product which is coded for by the inserted recombinant DNA sequence.

A cell which expresses human transferrin is provided by first, preparing at least one first nucleic acid sequence which is complementary to at least one second nucleic acid sequence wherein the second nucleic acid sequence codes for human transferrin, followed by transforming an appropriate host cell with the first nucleic acid sequence so prepared. A cellular clone actively expressing human transferrin can then be selected from the group of cells so transformed.

Although genetically engineered transferrin may be provided in the above manner by providing the recombinant expression vector directly, it may be more convenient to provide a recombinant DNA transfer vector, such as pBR322, that includes a DNA sequence which is complementary to a nucleic acid sequence which codes for human transferrin. In this manner, a recombinant expression vector containing the recombinant transferrin gene DNA may then be constructed using the recombinant Transferrin gene DNA sequence contained within such recombinant transfer vector. A recombinant DNA transfer vector as used herein refers to a cloning vector which may be used in transferring cloned recombinant DNA sequences from one host to another and are particularly useful for preparing recombinant clone banks. Examples of transfer vectors include pBR322 and its numerous derivations. It should be noted that transfer vectors can be used for expressing a cloned gene, however such vectors are generally not as efficient as the expression vectors for such purposes.

Recombinant DNA vectors as used herein may be either recombinant DNA transfer vectors or recombinant DNA expression vectors. Such recombinant DNA vectors include plasmids (which are extrachromasomally replicating circular DNA's), bacteriophage (such as the lambda phage), and human viruses such as SV-40 which have been adapted for both transfer and expression of recombinant DNA sequences (see, e.g., Okayama and Berg, infra.).

One method for preparing at least one nucleic acid sequence which is complementary to at least one second nucleic acid sequence which codes for human transferrin entails enzymatically copying total human messenger RNA (mRNA), preferably human liver mRNA, into complementary DNA (cDNA) sequences. In this manner, at least one of the cDNA sequences so obtained will contain the necessary genetic sequence information to code for human transferrin mRNA. A recombinant clone which receives the cDNA which is complementary to the gene coding for human transferrin can then be selected using selection techniques known to those skilled in the art, for example, antibody screening where the transferrin cDNA is cloned into the expression vector, or a transferrin-specific nucleic acid probe where the transferrin cDNA is cloned into a transfer vector.

The preferred enzyme for enzymatically copying human mRNA into complementary nucleic acid sequences is the enzyme reverse transcriptase. However, other nucleic acid polymerizing enzymes, such as DNA polymerase I, may be useful. Nucleic acid sequences capable of coding for human transferrin may be prepared in other ways as well, including synthetic preparation of the appropriate DNA sequence, using the nucleic acid sequence or amino acid sequence of Table 1 as a guide. Synthetically prepared transferrin gene sequences should function identically with transferrin gene sequences which are enzymatically prepared.

Although for commercial preparation of recombinant transferrin, it may be more appropriate to provide the recombinant transferrin cDNA in a bacterial host/vector system, it is nevertheless possible to provide the cDNA in a eukaryotic host/vector system using the techniques described or referred to herein.

DETAILED DESCRIPTION OF THE PREFERRED EMBODIMENTS

The present invention describes the isolation and nucleic acid sequence of the human transferrin cDNA gene and methods whereby human Transferrin may be produced through recombinant DNA technology. In general, the production of recombinant human transferrin is achieved by, first, construction of a recombinant clone bank, using a suitable host/vector system, which contains recombinant DNA sequences which are complementary to human messenger RNA (mRNA) sequences, followed by selection of recombinant clones which contain DNA sequences that are complementary to human transferrin mRNA.

Once a recombinant clone which contains the entire transferrin gene coding sequence (i.e.—sequences capable of coding for the entire transferrin protein) has been isolated, this transferrin coding sequence can be introduced into a host/vector system which is capable of "expressing" the protein product for which the transferrin sequences code.

Although the present invention is described by way of the above two-step approach, there is no reason why the invention could not be successfully practiced by preparing an "expression" gene bank directly, using an appropriate host/vector expression system, for example, the pIN-III vectors of Masui et al. (1983), infra., or the SV-40 derived eukaryotic vector of Okayama and Berg (1983) Mol. Cell. Biol., 3:280, incorporated herein by reference. The Okayama vector permits expression in eukaryotic cells. This would bypass the extra step of transferring the recombinant transferrin sequences from the transfer vector to the expression vector. However, it is often easier to obtain or prepare recombinant gene banks in host/vector systems which are not well suited for expressing the cloned protein gene. For example, plasmid pBR322 and related vectors have well characterized drug resistance genes which facilitate the selection of recombinant bacteria. The cDNA is generally inserted into the drug resistance gene coding region of these vectors, thereby destroying resistance to a particular antibiotic and thus providing a selection means. However, since the cDNA is being inserted into the middle of another gene, i.e., the resistance gene, it is not generally well suited to expressing the cDNA protein. Furthermore, the excision of a recombinant gene from one host/vector system followed by insertion of the sequence into an expression host/vector system involves techniques which are well understood and can be readily accomplished by those skilled in the art.

EXAMPLE I

ISOLATION OF A RECOMBINANT CLONE WHICH CONTAINS A DNA SEQUENCE WHICH CODES FOR HUMAN TRANSFERRIN

A recombinant microorganism containing a DNA sequence which is complementary to the coding sequence of the human transferrin gene was isolated by hybridization selection from a human cDNA (complementary DNA) recombinant clone library constructed in *E. coli*. This clone library was hybridization screened using a mixture of sixteen radiolabeled oligonucleotides corresponding to all of the possible DNA sequences coding for a known region of the human Transferrin protein sequence. Positive hybridization of the radiolabeled oligonucleotide mixture identified twenty cDNA clones. One of these, designated Tf, was found to contain the entire Transferrin gene coding sequence. The detailed steps used to isolate Tf are as follows.

Construction of the Human Recombinant cDNA Library

The human recombinant cDNA library used by the present inventors to isolate the human transferrin cDNA was constructed as described in Prochownik, et al., (1983) *J. Biol. Chem.*, 258:8389-8394 (incorporated herein by reference) and provided by Stuart H. Orkin, Harvard Medical School, Boston, MA. This clone bank was constructed by insertion of sized human liver cDNA into the ampicillin resistance gene of pKT218, an *E. coli* transfer vector derivative pBR322 described in Talmadge, et al. (1980), *Proc. Natl. Acad. Sci. U.S.A.*, 77:3369-3373.

To practice the present invention, it is not necessary that this particular human recombinant cDNA clone bank be utilized. Virtually any human cDNA clone bank constructed in any host/vector system can be utilized. Similarly, there is no requirement that the cDNA clone bank be constructed in a bacterial plasmid. For example, numerous lambda bacteriophage can be utilized in practicing the present invention without undue experimentation by one skilled in the art. The clone bank may also be constructed in a eukaryotic host/vector system such as that described by Okayama/Berg, supra. Due to the relatively low abundance of transferrin messenger RNA in non-hepatic tissues, it is recommended that the recombinant clone bank utilized be constructed using human liver RNA sequences for priming cDNA synthesis. Although not crucial, this will avoid the extra work of screening numerous negative recombinant clones.

Preparation of Transferrin-specific DNA Hybridization Probes for Screening the Human cDNA Recombinant Clone Bank In order to identify those recombinant clones containing human transferrin gene cDNA sequences, DNA hybridization probes complementary to a region of the human transferrin gene were synthesized. The nucleic acid sequences of the transferrin gene-specific hybridization probes used in the present invention were predetermined through consideration of a published amino acid sequence for the transferrin protein (see MacGillivray, et al. (1983), *J. Biol. Chem.* 258:3543-3553). Transferrin-specific DNA sequences could thereby be extrapolated from the published amino acid sequence by application of the genetic code. Due to the fact that the genetic code is redundant for several amino acids, a number of hybridization probes must necessarily be synthesized to take into account all of the possible DNA sequences corresponding to the published amino acid sequence.

The sequence of amino acid residues 309-314 (Met-Asn-Ala-Lys-Met-Tyr) of human transferrin, as determined by MacGillivray, et al., supra, was chosen for construction of the corresponding 17-nucleotide-long DNA probes. In particular, it was determined that thor sixteen possible sequences which correspond to ami residues 309-314 as follows:

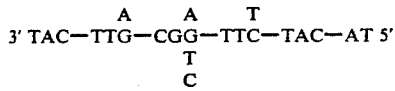

Thus, there are two possible codons for Asparagine (TTG and TTA), four for Alanine (CGG, CGA, CGC) and two for lysine (TTT and TTC). In all, works out to 16 possible combinations.

This mixture of 16 DNA hybridization, complementary to a particular region within the transferrin gene sequence, were synthesized by the solid-phase phosphite triester method of Alvarado-Urbina, et. al. (1981), *Science*, 214:20-274 (incorporated herein by reference), by BioLogicals (Ottawa, Canada).

Screening of the Recombinant cDNA Clones to Identify and Isolate Those Containing the entire Human Transferrin Gene Coding Sequence The cDNA library described above was onto L-agar plates containing 10 ug/ml of After overnight growth, the colonies were to nitrocellulose filters and incubated on L-ager plates containing 250 ug/ml of chloramphenicol to promot.amplification. The filters were prepared for hybridization as described by Grunstein and Hogness (1975) *Proc. Natl. Acad. Sci. U.S.A.*, 72:3961-3965, incorporated herein by reference.

The filters were hybridized at 37° C. with the $^{32}$P-labeled oligonucleotide mixed probes as described by Wallace, et al., (1981) *Nucleic Acids Res.*, 9:879-894, incorporated herein by reference. The hybridization mixture contained 0.9 M NaCl, 0.09 M Tris-HCl (pH 7.5), 0.006 M EDTA, 0.5% NaDodSO$_4$, 5x Denhardt's solution (1x=0.02% polyvinyl pyrrolidine, 0.02% bovine serum albumin, and 0.02% Ficoll), 100 ug of denatured *E. coli* DNA per ml, and 6.4 ng of 5' end-labeled oligonucleotide mixed probes per ml having a specific activity of approximately 7 x 10$^8$ cpm/ug.

By this procedure, twenty cDNA clones were isolated from the human liver cDNA recombinant clone bank which contained sequences that hybridized with the mixed DNA hybridization probes prepared above. One of these clones, designated as clone Tf, contained the entire human transferrin coding sequence as determined by DNA sequence analysis (see Example II). This clone has been deposited with the American Type Culture Collection, Rockville, MD., as ATCC number 53106 (TfR27A/HB101) and contains plasmid Tf which includes the entire coding sequence of the human transferrin cDNA inserted into the Pst I site of the ampicillin resistence gene of pKT218 as described above.

It is important to the successful practice of the present invention, that the transferrin gene so-isolated, contain the entire coding sequence for the structural protein. This is necessary because a clone which is defective in that it lacks certain regions of the transferrin gene coding sequence cannot be used to produce a complete and functional transferrin protein molecule. Thus, to reduce the number of false-negative clones (i.e., clones which do not contain the full-length coding sequence) identified, it is suggested that a hybridization probe be constructed which corresponds to an amino-terminal region of gene. This is due to the fact that incomplete cDNA clones will be incomplete in terms of those sequences which code for the amino-terminus of the resultant peptide. Therefore, by screening with probes which favor the amino terminal codons, one reduces the number of false-positives identified. The hybridization probes used by the present inventors were sufficiently amino-terminal directed to identify a recombinant clone bearing a full length transferrin gene.

EXAMPLE II

SEQUENCE OF THE TRANSFERRIN-CODING DNA AND ITS CORRESPONDING PROTEIN

DNA sequencing technology was used to sequence the transferrin-cDNA insert in plasmid Tf and thereby predict the proper amino acid sequence of human transferrin.

Preparation of Plasmid DNA

Bacterial clones were grown in M9 medium supplemented with 0.2% Casamino acids (Difco), 0.5% glucose, 0.01 M MgSO$_4$, and 5 ug of tetracycline per ml. When the optical density of the culture reached 0.8 OD$_{600}$, 100 ug of chloramphenicol per ml was added and the culture was incubated overnight. Plasmid DNA was isolated as described by Blaira, et al. (1972), *Proc. Natl. Acad. Sci. U.S.A.*, 69:2518-2572, incorporated herein by reference, and purified on two consecutive ethidium bromide/CsCl gradients.

Restriction Endonuclease Mapping and DNA Sequence Determination

Restriction endonuclease fragments were first labeled either at the 5' end with [$\gamma$-$^{32}$ATP] by using T4 polynucleotide kinase (as described by Maniatis, et al. (1982) *Molecular Cloning, A Laboratory Manual*, Cold Spring Harbor Laboratory, Cold Spring Harbor, New York, pp. 122-127, incorporated herein by reference), at the 3' end with [$\gamma$-$^{32}$-P]dNPTs by using the Klenow fragment of *E. coli* polymerase I, or at the 3' end with cordycepin [$\gamma$-$^{32}$P]triphosphate by using terminal deoxynucleotide transferase (by the method of Tu and Cohen (1980), *Gene*, 10:177-183, incorporated herein by reference). The labeled DNA fragments were then cleaved with a second endonuclease, and the uniquely labeled fragments were separated by polyacrylamide or agarose gel electrophoresis. Labeled DNAs were recovered by electroelution and subjected to sequence analysis by the method of Maxam and Gilbert (1980) *Methods Enzymol.* 1 65:498-560, incorporated herein by reference. Homology of nucleotide sequences in the NH$_2$ and COOH domains was evaluated by calculation of an "accident probability," P$_a$, the probability that a homology equal to or greater than that being considered might arise accidentally. A homology over 100 nucleotides with a P$_a$ of $<7\times10^{-4}$ was considered significant.

The DNA Coding Sequence and Corresponding Amino Acid Sequence of the Human Transferrin Gene as Exemplified by Clone Tf The DNA sequence determined for the transferrin cDNA insert of recombinant clone Tf is depicted in Table I. Also shown in Table I is the predicted amino acid sequence which corresponds to the DNA sequence of human transferrin.

The amino acid sequence predicted for human transferrin in this manner demonstrates that the transferrin amino acid sequence previously known in the art, as exemplified by MacGillivray, et al., supra, was inaccurate and incomplete. For example, the nucleotide sequence predicted glutamine at 245 residue, instead of glutamic acid, and predicted asparagine, instead of aspartic acid, at residue 417. Aspartic acid, instead of asparagine, was deduced at residue 310. Residues 361 and 362 were aspargine-serine instead of serine-aspartic acid. Residue 539 was proline, instead of threonine, and residue 542 was threonine, instead of proline. Residues 572 and 653 were predicted to be glutamic acid, instead of glutamine. Such inaccuracies are most likely due to commonly encountered drawbacks in the techniques used for amino acid sequence analysis. However, from a practical standpoint, due to the presence of inaccuracies and incompleteness of the prior art sequence, a transferrin protein which has been constructed based on a consideration of this prior sequence would not function as human transferrin should.

Note that Table I only displays the actual sequence of the Transferrin cDNA which was determined by DNA sequence analysis of the Transferrin cDNA insert of plasmid Tf. Due to the redundancy present in the genetic code, numerous other sequences may be constructed which code for the same human transferrin amino acid sequence. Therefore, any nucleic acid sequence which could code for the human transferrin protein as depicted in Table I are meant to be included within the scope of the present invention.

TABLE I

```
TGT GCT CGC TGC TCA GCG CGC ACC CGG AAG ATG AGG CTC GCC GTG GGA GCC CTG GTC TGC GCC GTC CTG GGG CTG TGT CTG GCT
                                                              -19                                              -1
                                                              MET ARG LEU ALA VAL GLY ALA LEU VAL CYS ALA VAL LEU GLY LEU CYS LEU ALA

GTC CCT GAT AAA ACT GTG AGA TGG TGT GCA GTG TCG GAG CAT GAG TCG CAG AGT TTC CGC GAC AGT TTC CGC CAT ATG AAA AGC GTC ATT
 1                                          10                                          20                           30
VAL PRO ASP LYS THR VAL ARG TRP CYS ALA VAL SER GLU HIS GLU ALA THR LYS CYS GLN SER PHE ARG ASP HIS MET LYS SER VAL ILE

CCA TCC GAT GGT CCC AGT GTT GCT GTT TGT GTG AAG AAA GCC TCC TAC CTT GAT TGC ATC AGG GCA ATT GCG AAC GAA GCG GAT GCT GTG
                                40                                          50                                          60
PRO SER ASP GLY PRO SER VAL ALA VAL CYS VAL LYS LYS ALA SER TYR LEU ASP CYS ILE ARG ALA ILE ALA ALA ASN GLU ALA ASP ALA VAL

ACA CTG GAT GCA GGT TTG GTG TAT GAT GCT TTG CCT AAT AAC CTG AAG CCT GTG GCA GAG TTC TAT GGG TCA AAA GAG GAT
                    70                                          80                                          90
THR LEU ASP ALA GLY LEU VAL TYR ASP ALA LEU PRO ASN ASN LEU LYS PRO VAL ALA GLU PHE TYR GLY SER LYS GLU ASP

CCA CAG ACT TTC TAT TAT GCT GTT GTG AAG GAT AGT GGC TTC CAG ATG CAG CTT CGA GGC AAG TCC TGC CAC ACG
                    100                                         110                                         120
PRO GLN THR PHE TYR TYR ALA VAL VAL LYS ASP SER GLY PHE GLN MET GLN LEU ARG GLY LYS SER CYS HIS THR

GGT CTA GGC AGG TCC GCT GGG TGG AAC ATC CCC ATA GGC TTA CTT TAC TGT GCC CCA CGT AAA CCT CTT GAG AAA GCA GTG
                    130                                         140                                         150
GLY LEU GLY ARG SER ALA GLY TRP ASN ILE PRO ILE GLY LEU LEU TYR CYS ALA PRO ARG LYS PRO LEU GLU LYS ALA VAL

GCC AAT TTC TTC TCG GGC AGC TGT GCC CCT TGT GCG GAT GGG ACG GAC TTC CAA CTG TGT CAA CTG TGT CCA GGG TGT TGC TCC
                    160                                         170                                         180
ALA ASN PHE PHE SER GLY SER CYS ALA PRO CYS ALA ASP GLY THR ASP PHE PRO GLN LEU CYS GLN LEU CYS PRO GLY CYS SER

ACC CTT AAC CAA TAC TTC GGC TAC TTC GGA GCC TTC AAG TGT CTG AAG GAT GGT GCT GGG GCC TTT GTC AAG CAC ACT ATA
                    190                                         200                                         210
THR LEU ASN GLN TYR PHE GLY TYR PHE GLY ALA PHE LYS CYS LEU LYS ASP GLY ALA GLY ASP VAL ALA PHE VAL LYS HIS SER THR ILE

TTT GAG AAC TTG GCA AAC AAG GCT GAC AGG GAC CAG TAT GAG CTT CTG TGC CTA GAC AAC ACC CGG AAG CCG GTA GAT GAA TAC AAG GAC
                    220                                         230                                         240
PHE GLU ASN LEU ALA ASN LYS ALA ASP ARG ASP GLN TYR GLU LEU LEU CYS LEU ASP ASN THR ARG LYS PRO VAL ASP GLU TYR LYS ASP

TGC CAC TTG GCC CAG GTC CCT TCT CAT ACC GTC GCC CGA AGT ATG GGC AAG GAG GAC TTG ATC TGG GAG CTT CTC AAC CAG GCC
                    250                                         260                                         270
CYS HIS LEU ALA GLN VAL PRO SER HIS THR VAL VAL ALA ARG SER MET GLY LYS GLU ASP LEU ILE TRP GLU LEU LEU ASN GLN ALA

CAG GAA CAT TTT GGC AAA GAC AAA TCA CAA CTA TTC CAA CTT CCT CAT GAG TCT CCT CAT GGG AAG CTG TTT CTG CTC TTC AAG TCT GCC CAC
                    280                                         290                                         300
GLN GLU HIS PHE GLY LYS ASP LYS SER GLN LEU PHE GLN LEU PHE SER SER PRO HIS GLY LYS ASP LEU PHE LYS LEU PHE SER SER ALA HIS

GGG TTT TTA AAA GTC CCC CCA CAG ATG GAT GCC AAG ATG TAC CTG ACT GAG TAT CGG CAA ATC CGG AAG CTA CGG AAG CAA GGC ACA
                    310                                         320                                         330
GLY PHE LEU LYS VAL PRO PRO ARG MET ASP ALA LYS MET TYR LEU GLY TYR TYR GLU TYR GLN TYR VAL THR ALA ILE ARG ASN LEU ARG GLU GLY THR

TGC CCA GAA GCC ACA ACA GAT GAA TGC AAG CCT GTG AAG AGG CAC AGC CTG AAG CAC GAG CTC AAG TGT GAT GAG TGG AGT GTT
                    340                                         350                                         360
CYS PRO GLU ALA PRO THR ASP GLU CYS LYS PRO VAL LYS ARG HIS SER LEU LYS HIS GLU ARG LEU LYS CYS ASP GLU TRP SER VAL
```

TABLE I-continued

```
AAC AGT GTA GGG AAA ATA GAG TGT GTA TCA GCA GAG ACC ACC GAA GAC TGC ATC GCC AAG ATC ATG AAT GGA GAA GCT GAT GCC ATG AGC
ASN SER VAL GLY LYS ILE  GLU CYS VAL SER ALA GLU THR THR GLU ASP CYS ILE ALA LYS ILE MET ASN GLY GLU ALA ASP ALA MET SER
                                                              370                                 380                                  390
TTG GAT GGA GGG TTT GTC TAC ATA GCG GGC AAG TGT CTG GGT CTG GTG CCT GTG GCA AAC TAC AAT AAG AGC GAT AAT TGT GAG GAT
LEU ASP GLY GLY PHE VAL TYR ILE  ALA GLY LYS CYS LEU GLY LEU VAL PRO VAL ALA ASN TYR ASN LYS SER ASP ASN CYS GLU ASP
                        400                                   410                                 420
ACA CCA GAG GCA GTT GCT GTA GCA GTG TAT TTT GCT GTA GCA GTG GTG AAG AAA TCA GCT TCT GAC AAT CTG AAA GGC AAG TCC TGC
THR PRO GLU ALA VAL ALA VAL ALA VAL TYR PHE ALA VAL ALA VAL VAL LYS SER ALA SER ASP ASN LEU LYS GLY LYS SER CYS
                                           430                                   440                              450
CAT ACG GCA GTT GGC AGA ACC GGT GGC TGG CAA ATC CCC ATG GGC CTC TAC AAT AAG ATC AAC CAC TGC AGA TTT GAT GAA TTT TTC
HIS THR ALA VAL GLY ARG THR GLY GLY TRP GLN ILE  PRO MET GLY LEU TYR ASN LYS ILE  ASN HIS  CYS ARG PHE ASP GLU PHE PHE
                             460                                    470                                   480
AGT GAA GGT TGT GCC CCT GGG TCT AAG AAA GAC TCC AGT CTC TGT ATG GGC TCA GCC CTA AAC CTG TGT GAA CCC AAC AAC
SER GLU GLY CYS ALA PRO GLY SER LYS  LYS  ASP SER SER LEU CYS MET GLY SER ALA LEU ASN LEU CYS GLU PRO ASN ASN
                       490                                  500                                    510
AAA GAG GGA TAC TAC GGC GTC TGT CTG GTT GAG AAG GAT GTG GCC TTT GTG AAA CAC CAG CAG ACT CCA CAG
LYS GLU GLY TYR TYR GLY VAL CYS LEU VAL GLU LYS ASP VAL ALA PHE VAL LYS HIS  GLN THR VAL PRO GLN
                                            520                                   530                 540
AAC ACT GGG GGA AAA AAC CCT GAT CCA TGG GCT AAG AAT GAA AAA GAC TAT GAG TTG CTG TGC CTT GAT GGT ACC AGG AAA CCT
ASN THR GLY GLY LYS  ASN PRO ASP PRO TRP ALA LYS  ASN GLU LYS  ASP TYR GLU LEU LEU CYS LEU ASP GLY THR ARG LYS PRO
                       550                                    560                                     570
GTG GAG GAG TAT GCG AAC TGC CAC CTG GCC AGA GCC CCG AAT CAC CAC GTG GTC TGC ACA GAA GAT AAG GAA GCT TGC CAC AAG ATA
VAL GLU GLU TYR ALA ASN CYS HIS  LEU ALA ARG ALA PRO ASN HIS  HIS  VAL THR ARG LYS ASP LYS  GLU ALA CYS VAL HIS LYS ILE
                                            580                                   590                                   600
TTA CGT CAA CAG CAG CAC CTA TTT GGA AGC AGC ACT GAC TCG GGC AAC TTT  TGT TTG TTC CGG TCG GAA ACC AAG GAC CTT CTG
LEU ARG GLN GLN GLN HIS  LEU PHE GLY SER SER THR ASP SER GLY ASN PHE CYS LEU PHE ARG SER GLU THR LYS ASP LEU LEU
                              610                                   620                                    630
TTC AGA GAT GAC ACA GTA TGT TTG GCC AAA CTT CAT GAC AGA AAC TAT GAA AAA TAC TTA GGA GAA GAA TAT GTC AAG GCT GTT GGT
PHE ARG ASP ASP THR VAL CYS LEU ALA LYS  LEU HIS  ASP ARG ASN TYR GLU LYS  TYR LEU GLY GLU GLU TYR VAL LYS  ALA VAL GLY
                        640                                     650                                     660
AAC CTG AGA AAA TGC TCC ACC TCA CTC CTG GAA GCC TGC ACT TTC CGT AGA TAA AAT CTC AGA GGT GCC ACC AAG GTG
ASN LEU ARG LYS  CYS SER THR SER LEU LEU GLU ALA CYS THR PHE ARG ARG PRO
                                             670                                 679
AAG ATG ACG CAG ATG ATC CAT GAG TTT GCC CTG GTT TCA CTG GCC CAA GTG GTT TGT GCT AAC CAC GTC TGT CTT CAC AGC TCT GTG

TTG CCA TGT GTG CTG AAC AAA AAA AAA TAA AAA TTA TTA TTG ATT TTA TAT TTC PolyA(29)
```

EXAMPLE III

EXPRESSION OF THE RECOMBINANT TRANSFERRIN GENE

The instant example, and embodiments presented herein, are prophetic in that procedures are described which the present inventors believe represent preferred embodiments for expressing the recombinant Transferrin gene described in the preceeding examples. Although the procedures described in the present example have not been specifically applied to the recombinant Transferrin gene, the present inventors understand that the technology herein described is well known in the art and that these procedures may be accomplished without undue experimentation.

Prokaryotic systems have been shown to express many eukaryotic genes at a high level of expression. The present inventors plan to express the recombinant human Transferrin gene, isolated and cloned as described in the preceding examples, in *E. coli* cells. One preferred vector for obtaining expression of this recombinant gene is the pIn vector which utilizes the very efficient *E. coli* lipoprotein promoter as well as other portions of the lipoprotein gene, lpp. The pIn vector is described in detail in Masui, Y., Coleman J, and Inouye, M. (1983) in *Experimental Manipulation of Gene Expression*, ed by M. Inouye, incorporated herein by reference. The lipoprotein which is F8 amino acid residues in length, is the most abundant protein in *E. coli* in terms of the number of molecules produced. Therefore, it is considered that the lpp gene has one of the strongest promoters in *E. coli*.

The lpp gene mRNA is only 332 bases long (see, e.g., Nakamura, et al. (1980) *Proc. Natl. Acad. Sci. U.S.A.*, 77:1367–1373). The two-thirds of the mRNA from its 3' end is highly enriched with stable stem-and-loop structures, and its 3' end is typical of a rho-independent transcription termination signal. Expression of the lpp gene is constitutive, and its promoter region (45 base pairs) is extremely A-T rich. Furthermore, the space region approximately 160 base pairs upstream from the promoter region is also A-T rich. These features are thought to play important roles in efficient transcription, translation and high stability of the lpp mRNA. These structural considerations were taken into consideration in constructing the pIn expression vectors.

One pIn vector for obtaining expression of the recombinant Transferrin gene is pIn-III, described in detail by Masui, et al. (1983) in *Experimental Manipulation of Gene Expression*, edited by M. Inouye, page 15, incorporated herein by reference. (The pIN-III series is on deposit with the ATCC as pIN-III A/NRRL-B under the accession numbers 15024, 15025, 15038, 15017 and 15236). In addition to the strong lpp promoter, pIn-III contains the lac UV5 promoter-operator inserted downstream of the lpp promoter. This arrangement represses transcription in the absence of a lac inducer, if the host strain can produce enough lac repressor molecules. Since the lac I gene is also included in the same plasmid, the expression of the cloned gene can therefore be regulated by the lac repressor produced by the vector itself. Therefore, any *E. coli* host strain may be used for this vector.

To facilitate the cloning and expression of a foreign DNA fragment in this vector, unique Eco RI, Hind III and Bam HI sites were created by inserting a 22 base pair DNA sequence containing these sites, into the lpp gene. Furthermore, this sequence was inserted in three different reading frames so that any DNA fragment can be expressed by choosing one of the three resultant cloning vectors. For a complete description of this work, see Nakamura, K. and Inouye, M. (1982) *EMBO J.*, 1:771–775, incorporated herein by reference.

Since the recombinant transferrin cDNA gene described in EXAMPLES I and II above, is inserted in the Pst I site of plasmid pKT 218, the cDNA insert can be excised from the plasmid by restriction endonuclease digestion with Pst I. The recombinant transferrin gene so-excised, will appear as two separate Pst I fragments, one having a 1.5 kilobase pair length and the other, 0.8 kilobase pairs. These two fragments can be ligated by treatment with DNA ligase using the procedure of Sugino, A., Goodman, H.M., Heyneker, H.L., Shine, J., Boyer, H.W., and Cozzarelli, N.R. (1977) *J. Biol. Chem.*, 252:3987, incorporated herein by reference, to produce the full-length transferrin cDNA, free from the original pKT 218 vector.

The resultant overhanging 3' ends of the free cDNA can then be modified to cohesive Eco RI ends. This is done by first generating blunt ends by treatment with Bal 31 or S1 nuclease, for example, by the method of Legerski, R.J., Hodnett, J.L., and Gray Jr., H.B., (1978) *Nucleic Acid Research*, 5:1445, incorporated herein by reference. Since the human Transferrin cDNA has one internal Eco RI site, it is next necessary to "protect" this site from Eco RI endonuclease digestion by methylation of the site through treatment of the cDNA fragment with Eco RI methylase. This can be accomplished by the method of Maniatis, T., Hardison, R.C., Lacy, E., Lauer, J., O'Connell, C., Duon, D., Sim, G.K., and Efstratiadis, A. (1978) *Cell*, 15:687, incorporated herein by reference.

Following Eco RI methylation, Eco RI linkers may be used to add Eco RI recognition sites to pIn-III vectors exhibiting each of the three different reading frames ($C_1$, $C_2$, $C_3$) Each vector can be tried separately to obtain the correct reading frame for the recombinant Transferrin gene. Alternatively, the three reading-frame vectors may be mixed prior to ligating in the Transferrin cDNA. Regardless of the different reading frames, all of the cloned gene products will have identical signal peptides plus eight amino acid residues at their amino terminus. Therefore, both ends of the methylated transferrin cDNA. The ligtation of Eco RI linkers can be accomplished by the method of Sugino, supra, incorporated herein by reference, and the cohesive termini generated by treatment with Eco RI.

The resultant human Transferrin cDNA, which contains an Eco RI site at both termini can then be ligated into the Eco RI site of pIn-III using the above ligation procedure. The three resultant hybrid protein will be secreted across the cytoplasmic membrane.

Numerous other expression vectors are known in the art and can be used for expressing the recombinant Transferrin gene. Table II is a partial list of commercially available expression vectors, all of which may be used in the practice of the present invention. The foregoing genetic manipulations with respect to insertion of the recombinant Transferrin gene into the pIN vector are equally applicable to insertion into the vector systems listed in Table II with only very minor modifications which will be apparent to those skilled in the art. In addition, such modifications with respect to expression using these vectors will particularly be apparent in light of the directions which accompany these vectors from the supplier. All vectors listed in Table II are available from Pharmacia, Uppsala, Sweden.

TABLE II

| CATALOGUE NO. | PLASMID | PROMOTER | HOST USED |
|---|---|---|---|
| 27-4916-01 | pUC series | lac | E. coli (lac$^-$) |
| 27-4935-01 | pKK223-3 | Trp-lac | E. coli JM105 (lac iQ) |
| 27-4932-01 | pDR540 | Trp-lac | E. coli JM103 (lac iQ) |
| 27-4930-01 | pDR720 | Trp | E. coli (C600) |

The *E. coli* host which is chosen for expression of the recombinant human transferrin, can be transformed using the procedure of Mandel, M. and Higa, A. (1970) *J. Mol. Biol.*, 53:154, incorporated herein by reference. The resultant transformants can then be screened for transferrin expression by immunodetection using the procedure of Kemp, D.J. and Cowman, A.F. (1981) *Proc. Natl. Acad. Sci. U.S.A.* (1981) 78:4520, incorporated herein by reference, using commercially available transferrin antibody (*Accurate Chemical & Scientific*, Westbury, N.Y.).

Although the present invention has been described in terms of preferred embodiments, those of skill in the art will recognize that various modifications may be undertaken without departing from the scope of the appended claims. For example, numerous alternatives and modifications are known for the various genetic and enzymatic manipulations described herein and the present inventors consider such modifications to be within the scope of the present invention. In addition, although EXAMPLE III is described in terms of a prokaryotic host/vector expression system, there is no reason why the human Transferrin gene described herein cannot be expressed in one of the several eukaryotic host/vector systems known in the art. Accordingly, these and all other modifications are considered to be within the scope of the appended claims.

What is claimed is:

1. A recombinant DNA vector comprising a DNA sequence encoding human transferrin.

2. The recombinant DNA vector of claim 1 wherein the DNA sequence is defined further as being a cDNA sequence which is complementary to human transferring mRNA.

3. The recombinant DNA vector of claim 1 wherein the DNA sequence is defined further as being the DNA sequence of Table 1.

4. The recombinant DNA vector of claim 2 wherein the DNA sequence is defined further as being the DNA sequence of Table 1.

5. The recombinant DNA vector of claim 1 wherein the DNA sequence is defined further as a DNA sequence encoding the amino acid sequence of Table 1.

6. The recombinant DNA vector of claim 1 defined further as being a recombinant plasmid.

7. The recombinant DNA vector of claim 5 or claim 6 defined further as being plasmid Tf.

8. The bacterial strain bearing a recombinant DNA vector comprising a DNA sequence encoding human transferring.

9. The bacterial strain of claim 8, wherein the DNA sequence is defined further as being a cDNA sequence which is complementary to human transferrin mRNA.

10. The bacterial strain of claim 8, wherein the DNA sequence is defined further as being the DNA sequence of Table 1.

11. The bacterial strain of claim 8, wherein the bacterial strain is identified as ATCC number 53106.

12. A substantially purified DNA molecule comprising a DNA sequence encoding human transferrin.

13. The DNA molecule of claim 12 wherein the DNA sequence is defined further as being a cDNA sequence which is complementary to a human transferrin mRNA.

14. The DNA molecule of claim 12 wherein the DNA sequence is defined further as being the DNA sequence of Table 1.

15. The DNA molecule of claim 13 wherein the DNA sequence is defined further as being the DNA sequence of Table 1.

16. The DNA molecule of claim 12 wherein the DNA sequence is defined further as being a DNA sequence encoding the amino acid sequence of Table 1.

* * * * *

UNITED STATES PATENT AND TRADEMARK OFFICE
CERTIFICATE OF CORRECTION

PATENT NO.    :    5,026,651
DATED         :    June 25, 1991
INVENTOR(S)   :    Bowman, et al.

It is certified that error appears in the above-identified patent and that said Letters Patent is hereby corrected as shown below:

Claim 2, line 6, column 16, delete "transferring" and replace with --transferrin--.

Claim 8, line 22, column 16, delete "transferring" and replace with --transferrin--.

Signed and Sealed this

Twenty-fourth Day of November, 1992

Attest:

DOUGLAS B. COMER

Attesting Officer       Acting Commissioner of Patents and Trademarks